(12) United States Patent
Klock et al.

(10) Patent No.: US 7,655,773 B2
(45) Date of Patent: Feb. 2, 2010

(54) ANTI-APOPTOTICALLY ACTIVE APATAMERS

(75) Inventors: Gerd Klock, Dieburg (DE); Mark A. Freyberg, Darmstadt (DE); Dirk Kaiser, Eppertshausen (DE)

(73) Assignee: CytoTools AG, Darmstadt (DE)

( * ) Notice: Subject to any disclaimer, the term of this patent is extended or adjusted under 35 U.S.C. 154(b) by 0 days.

(21) Appl. No.: 10/582,279

(22) PCT Filed: Dec. 10, 2004

(86) PCT No.: PCT/EP2004/014097

§ 371 (c)(1), (2), (4) Date: Jun. 9, 2006

(87) PCT Pub. No.: WO2005/056793

PCT Pub. Date: Jun. 23, 2005

(65) Prior Publication Data

US 2007/0117768 A1    May 24, 2007

(30) Foreign Application Priority Data

Dec. 11, 2003  (DE) ............................... 103 58 407

(51) Int. Cl.
C07K 14/47 (2006.01)
C07H 21/02 (2006.01)
C07H 21/04 (2006.01)

(52) U.S. Cl. .................................................. 536/23.1

(58) Field of Classification Search .................. None
See application file for complete search history.

(56) References Cited

U.S. PATENT DOCUMENTS

2005/0222020 A1  10/2005  Freyberg et al. .............. 514/12

FOREIGN PATENT DOCUMENTS

| DE | 101 63 130 | 10/2005 |
| WO | WO 02/26932 | 4/2002 |
| WO | WO03/039484 | * 5/2003 |
| WO | WO 03/054009 | 7/2003 |

OTHER PUBLICATIONS

Genbank—Thrombospondin-1 (TSP-1) sequence.*
TC1600 Memo—Interpreting claims with SEQ ID Nos.*
Agrawal, "Antisense Oligonucleotides Towards Clinical Trials," *Tibtech*, vol. 14, pp. 376-387, Oct. 1996.
Cerchia et al., "Nucleic Acid Aptamers in Cancer Medicine," *FEBS Letters*, vol. 528, pp. 12-16, Aug. 28, 2002.
Ellington et al., "Aptamers as Potential Nucleic Acid Pharmaceuticals," *Biotechnology Annual Review*, vol. 1, pp. 185-214, 1995.
Famulok, "Oligonucleotide Aptamers that Recognize Small Molecules," pp. 324-329.
Freyberg et al., "Proatherogenic Flow Conditions Initiate Endothelial Apoptosis via Thrombospondin-1 and the Integrin-Associated Protein," *Biochemical and Biophysical Research Communications*, vol. 286, pp. 141-149, 2001.
Gold et al., "Diversity of Oligonucleotide Functions," *Annu. Rev. Biochem.*, vol. 64, pp. 763-797, 1995.
Jayasena, "Aptamers: An Emerging Class of Molecules that Rival Antibodies in Diagnostics," *Clinical Chemistry*, vol. 45, No. 9, pp. 1628-1650, 1999.
Köhler et al., "Continuous Cultures of Fused Cells Secreting Antibody of Predefined Specificity," *Nature*, vol. 256, pp. 495-497, 1975.
Osborne et al., "Nucleic Acid Selection and the Challenge of Combinatorial Chemistry," *Chem. Rev.*, vol. 97, pp. 349-370, 1997.
Pieken et al., "Kinetic Characterization of Ribonuclease-Resistant 2'-Modified Hammerhead Ribozymes," *Science*, vol. 253, pp. 314-317, Jul. 19, 1991.
Ruckman et al., "2'-Fluoropyrimidine RNA-Based Aptamers to the 165-Amino Acid Form of Vascular Endothelial Growth Factor (VEGF 165)," *The Journal of Biological Chemistry*, vol. 273, No. 32, pp. 20556-20567, Aug. 7, 1998.
The Eyetech Study Group, "Preclinical and Phase 1A Clinical Evaluation of an Anti-VEGF Pegylated Aptamer (EYE001) for the Treatment of Exudative Age-Related Macular Degeneration," *The Journal of Retinal and Vitreous Diseases*, vol. 22, No. 2, pp. 143-151, 2002.

* cited by examiner

*Primary Examiner*—Janet L. Epps-Smith
*Assistant Examiner*—Scott D Long
(74) *Attorney, Agent, or Firm*—Marshall, Gerstein & Borun LLP

(57) ABSTRACT

The invention relates to anti-apoptotically active apatamers. The invention describes possible therapeutic and diagnostic applications for, among other things, treating arteriosclerosis, promoting the healing of wounds, treating AIDS, cancer, Alzheimer's disease, systemic lupus erythematosus as well a rheumatoid arthritis and other chronic inflammatory diseases.

6 Claims, 1 Drawing Sheet

SEQUENCE LISTING

```
<160> NUMBER OF SEQ ID NOS: 10

<210> SEQ ID NO 1
<211> LENGTH: 66
<212> TYPE: DNA
<213> ORGANISM: Artificial Sequence
<220> FEATURE:
<223> OTHER INFORMATION: Aptamer

<400> SEQUENCE: 1
gggagacgat attcgtccat caccggacgg gaccagaggt gccgctgtcc gactgaattc      60
tcgacc                                                                66

<210> SEQ ID NO 2
<211> LENGTH: 66
<212> TYPE: RNA
<213> ORGANISM: Artificial Sequence
<220> FEATURE:
<223> OTHER INFORMATION: Aptamer
<220> FEATURE:
<221> NAME/KEY: modified_base
<222> LOCATION: (1)..(66)
<223> OTHER INFORMATION: U = 2'-NH2-2'-desoxyuridin; C =
      2'-NH2-2'desoxycytidin
```

```
<400> SEQUENCE: 2
gggagacgau auucguccau caccggacgg gaccagaggu gccgcugucc gacugaauuc    60
ucgacc                                                              66

<210> SEQ ID NO 3
<211> LENGTH: 21
<212> TYPE: RNA
<213> ORGANISM: Artificial Sequence
<220> FEATURE:
<223> OTHER INFORMATION: Aptamer
<220> FEATURE:
<221> NAME/KEY: modified_base
<222> LOCATION: (1)..(21)
<223> OTHER INFORMATION: U = 2'-NH2-2'-desoxyuridin; C =
      2'-NH2-2'desoxycytidin

<400> SEQUENCE: 3
accggacggg accagaggug c                                             21

<210> SEQ ID NO 4
<211> LENGTH: 58
<212> TYPE: RNA
<213> ORGANISM: Artificial Sequence
<220> FEATURE:
<223> OTHER INFORMATION: Aptamer
<220> FEATURE:
<221> NAME/KEY: modified_base
<222> LOCATION: (1)..(58)
<223> OTHER INFORMATION: U = 2'-NH2-2'-desoxyuridin; C =
      2'-NH2-2'desoxycytidin

<400> SEQUENCE: 4
gggagacgau auucguccau caccggacgg gaccagaggu gccgcugucc gacaugga     58

<210> SEQ ID NO 5
<211> LENGTH: 30
<212> TYPE: RNA
<213> ORGANISM: Artificial Sequence
<220> FEATURE:
<223> OTHER INFORMATION: Aptamer
<220> FEATURE:
<221> NAME/KEY: modified_base
<222> LOCATION: (1)..(30)
<223> OTHER INFORMATION: U = 2'-NH2-2'-desoxyuridin; C =
      2'-NH2-2'desoxycytidin

<400> SEQUENCE: 5
accggacggg accagaggug ccgcuguccg                                    30

<210> SEQ ID NO 6
<211> LENGTH: 63
<212> TYPE: DNA
<213> ORGANISM: Artificial Sequence
<220> FEATURE:
<223> OTHER INFORMATION: Aptamer

<400> SEQUENCE: 6
gggagacgat attcgtccat cgggagcagg gaaggggggcc gctgtccgac tgaattctcg    60
acc                                                                 63

<210> SEQ ID NO 7
<211> LENGTH: 63
<212> TYPE: RNA
<213> ORGANISM: Artificial Sequence
<220> FEATURE:
<223> OTHER INFORMATION: Aptamer
<220> FEATURE:
```

```
<221> NAME/KEY: modified_base
<222> LOCATION: (1)..(63)
<223> OTHER INFORMATION: U = 2'-NH2-2'-desoxyuridin; C =
      2'-NH2-2'desoxycytidin

<400> SEQUENCE: 7
gggagacgau auucguccau cgggagcagg gaaggggcc gcuguccgac ugaauucucg      60
acc                                                                  63

<210> SEQ ID NO 8
<211> LENGTH: 18
<212> TYPE: RNA
<213> ORGANISM: Artificial Sequence
<220> FEATURE:
<223> OTHER INFORMATION: Aptamer
<220> FEATURE:
<221> NAME/KEY: modified_base
<222> LOCATION: (1)..(18)
<223> OTHER INFORMATION: U = 2'-NH2-2'-desoxyuridin; C =
      2'-NH2-2'desoxycytidin

<400> SEQUENCE: 8
gggagcaggg aagggggc                                                  18

<210> SEQ ID NO 9
<211> LENGTH: 30
<212> TYPE: RNA
<213> ORGANISM: Artificial Sequence
<220> FEATURE:
<223> OTHER INFORMATION: Aptamer
<220> FEATURE:
<221> NAME/KEY: modified_base
<222> LOCATION: (1)..(30)
<223> OTHER INFORMATION: U = 2'-NH2-2'-desoxyuridin; C =
      2'-NH2-2'desoxycytidin

<400> SEQUENCE: 9
ucgggagcag ggaaggggc cgcuguccga                                      30

<210> SEQ ID NO 10
<211> LENGTH: 28
<212> TYPE: RNA
<213> ORGANISM: Artificial Sequence
<220> FEATURE:
<223> OTHER INFORMATION: Aptamer
<220> FEATURE:
<221> NAME/KEY: modified_base
<222> LOCATION: (1)..(28)
<223> OTHER INFORMATION: U = 2'-NH2-2'-desoxyuridin; C =
      2'-NH2-2'desoxycytidin

<400> SEQUENCE: 10
cggacgggac cagaggugcc gcuguccg                                       28
```

ANTI-APOPTOTICALLY ACTIVE APATAMERS

BACKGROUND OF THE INVENTION

1. Field of the Invention

The present invention relates to anti-apoptotically active aptamers. The corresponding sequences are shown. The invention describes possible therapeutic and diagnostic applications.

2. Related Technology

Nucleic acid molecules (so-called aptamers) which specifically bind with certain target molecules (antigens), as well as methods for the manufacture and isolation of such aptamers, have already been very thoroughly described in the state of the art.

Such aptamers consisting of single-strand ssDNA or ssRNA possess very high affinities and specificities for the corresponding antigens. Up to now, nucleic acid ligands for metallic ions, organic compounds, peptides, proteins, or even complex structures such as viruses and cells have been isolated (Overview article: Gold et al., Annu. Rev. Biochem. 64 (1995), 763-797; Ellington and Conrad, Biotechnol. Annu. Rev. 1 (1995), 185-214; Famulok, Curr. Opin. Struct. Biol. 9 (1999), 324-329).

Aptamers are thus nucleic acids consisting of DNA or RNA which, due to their spatial structure, are able to bind specifically and with a high affinity to a certain target (Osborne, S. E. and Ellington, A. D., (1997). "Nucleic Acid Selection and the Challenge of Combinatorial Chemistry." Chem Rev 97(2): 349-370). Over the last years, a number of aptamers against medically relevant target proteins have been identified. Furthermore, it is expected that the use of nucleic acids for therapeutic and diagnostic purposes is now first really starting (Jayasena, S. D. (1999). "Aptamers: an emerging class of molecules that rival antibodies in diagnostics." Clin Chem 45(9): 1628-1650, Cerchia, L., Hamm, J., et al., (2002). "Nucleic acid aptamers in cancer medicine." FEBS Lett 528 (1-3): 12-16). The reasoning behind this new development involves the advantages which the identification and application of DNA or RNA molecules have in comparison with antibodies—which still dominate therapy and diagnosis in many fields to date.

The method for obtaining monoclonal antibodies (Köhler, G. and Milstein, C., (1975). "Continuous cultures of fused cells secreting antibody of predefined specificity." Nature 256 (5517): 495-497.) meant a large breakthrough for many fields of modern biology and medicine. In medical research, they play their most prominent role in the diagnostic field but, in the meantime, individual antibodies have also been granted approvals as drugs. If a certain protein, e.g. on the cell surface, has been identified as a target for diagnostic or therapeutic purposes and then a) its presence is to be identified for diagnostic purposes, or b) its function is to be blocked for therapeutic purposes, then to date, in both cases, the development of a monoclonal antibody was the most important and/or the fastest method. The development of low-molecular therapeutic agents is still a very long and tedious process. The disadvantages and limitations in the identification and production of antibodies are well known (Jayasena 1999), e.g. the necessity of carrying out the first immunisation with animal trials; the problem of availability and reproducibility of hybridoma cells over several years; or the high workload and enormous costs of antibody production.

An aptamer can be selected under specifically designed experimental conditions, such as e.g. those which are optimal for a diagnostic method (Jayasena 1999). Aptamers can be stored better over longer periods because, unlike proteins, they are not subjected to an irreversible denaturing but can be thermally renatured at any time. During the selection procedure, aptamers are usually synthesised enzymatically. For production on a larger scale however, they can also be synthesised chemically, therefore, in comparison with the production of monoclonal antibodies, their manufacture can be carried out with a much improved reproducibility (Jayasena 1999).

The modifications which lead to the stabilisation of DNA (Agrawal, S. (1996). "Antisense oligonucleotides: towards clinical trials." Trends Biotechnol 14(10): 376-387) or RNA (Pieken, W. A., Olsen, D. B., et al. (1991). "Kinetic characterization of ribonuclease-resistant 2'-modified hammerhead ribozymes." Science 253(5017): 314-317; Ruckman, J., Green, L. S., et al. (1998). "2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain." J Biol Chem 273(32): 20556-20567), have become established as routine methods in the synthesis of nucleic acids or their nucleotide precursors, so that today, the first aptamers can be tested in clinical trials (Eyetech Study Group (2002). "Preclinical and phase 1A clinical evaluation of an anti-VEGF pegylated aptamer (EYE001) for the treatment of exudative age-related macular degeneration." Retina 22(2): 143-152).

Apoptosis is a genetically coded "suicide program" which is induced in eukaryotic cells under certain physiological or pathological conditions. The induction of apoptosis must be extremely precisely regulated because a hyperactivity can lead to a degenerative illness. On the other hand, a reduced apoptosis induction can for example contribute to tumour progression.

Different low-molecular inductors of apoptosis have already been described. An important substance class are tumour cytostatics. However, the way in which these cytostatics or other substances induce apoptosis is not known in most cases.

The induction of apoptosis can for example take place via a series of so-called death receptors, i.e. receptors which contain a "Death Domain" (DD) such as CD95, TNF-RI, DR3, DR4 or DR5, which after binding their ligands induce apoptosis signal paths. For example, after binding the CD95 ligand, the CD95 receptor interacts with the adapter protein FADD/MORT1 whereby the "recruitment" and the activation of the protease FLICE/caspase 8 at the DISC "Death Inducing Signalling Complex" are induced. FADD and FLICE each contain "Death Effector Domains" (DED). The induction of apoptosis via these apoptosis signal paths is also possible from outside for example by administering cytotoxic substances, through radiation, viruses, withdrawal of growth factors or mechanical cell injuries. These possibilities of apoptosis induction are however accompanied by certain disadvantages. For example, the administration of toxins such as cytostatics or the radiation treatment of cancer cells can lead to resistance development and even to injury to normal healthy cells where no apoptosis induction whatsoever is desirable.

In general, the induction of apoptosis is proposed for the treatment, for example, of cancer or for preventing angiogenetic processes etc. Although inductors have already been described in this connection, they still demonstrate a number of disadvantages. For example, cytostatics are accompanied by severe side effects.

Pathological conditions where apoptosis has a negative effect and where suitable medical treatment involves the inhibition of apoptosis is also a subject of discussion.

An example of such a condition is arteriosclerosis. In particular, the inventors have already demonstrated earlier that apoptotic cells occur particularly in areas with arteriosclerotic plaque (especially: endothelial cells, smooth muscle cells), and that this occurrence is further enhanced by the disturbed flow conditions, i.e., it is flow-dependent (Freyberg et al., BBRC, 286, 141-149, 2001).

Also, substances which modulate apoptosis can be used to obtain a positive effect on wound healing. Further conditions under discussion which are associated with higher levels of apoptosis are AIDS, cancer and Alzheimer's disease, systemic lupus erythematosus, rheumatoid arthritis and other chronic inflammatory diseases.

There is therefore a large demand for substances which can have a positive or a negative influence on apoptosis. In the sense of the present invention, such substances which inhibit apoptosis are particularly preferred embodiments. It would be particularly favourable to inhibit the flow or force-dependent apoptosis also seen as a causal factor in arteriosclerosis and wound healing problems. A large demand thus remains for pharmaceutical formulations which contain such substances and which can be administered for the treatment of conditions in which the induction or the inhibition of apoptosis is indicated, in particular for the treatment of arteriosclerosis and the improvement of wound healing, as well as the treatment of AIDS, Alzheimer's disease and cancer.

In the older German patent application DE 101 63 130, the inventors of the present invention disclose peptides which inhibit or induce apoptosis.

GENERAL DESCRIPTION OF THE INVENTION

The invention provides further improved apoptotically active substances. In particular, the invention provides substances which can inhibit a TSP-1 induced apoptosis of eukaryotic cells, in particular in endothelial cells and fibroblasts and pharmaceutical preparations with which diseases such as arteriosclerosis, wounds, AIDS, Alzheimer's disease, cancer, systemic lupus erythematosus, rheumatoid arthritis and other chronic inflammatory diseases, in which the induction or the inhibition of apoptosis is indicated, can be treated.

Accordingly, the invention provides a nucleic acid comprising of a nucleic acid sequence selected from the group consisting of those shown in the SEQ ID NO: 1 to SEQ ID NO: 9.

A further embodiment of the present invention concerns functional variations of these nucleic acids.

These are, for the purposes of the present invention, nucleic acids which show a range of a least 6, preferably at least 10, very preferably at least 15 and most preferably of all at least 20 consecutive nucleotides, which exhibit at least 60%, preferably at least 70%, very preferably at least 80%, even more preferably at least 90% and most preferably of all at least 95% sequence identity to the sequences selected from the group consisting of: SEQ ID NO: 1 to SEQ ID NO: 9, and which, in the test procedure described below, exhibit an anti-apoptotic activity of at least 50% inhibition index, preferably at least 60%, very preferably at least 70%, even more preferably at least 80%, more preferably still at least 90% and most preferably of all at least 95%.

A further embodiment of the present invention concerns nucleic acids where, in 5'- and/or 3' direction, nucleotides attach to a nucleic acid sequence selected from the group consisting of SEQ ID NO: 1 to SEQ ID NO: 9. In particular, this extension comprises in each case of not more than 100, preferably not more than 70, especially preferably not more than 30, very especially preferably not more than 20 and most preferably of all not more than 10 nucleotides.

It goes without saying that here too functional variations of these extended nucleic acids are comprised in the sense of the above definition.

The aptamers of the present invention comprise preferably modifications which increase the stability of the nucleic acids according to the invention towards nuclease degradation. Preferably, here, 2'-NH$_2$-2'-deoxyuridine and/or 2'-NH$_2$-2'-deoxycytidine are used instead of the unmodified nucleotides uridine and cytidine.

For the purposes of the present invention, nucleic acids are understood as polymeric molecules which, in the case of RNA, are composed of the nucleotides adenosine (A), cytidine (C), uridine (U), guanosine (G) and, and is the case of DNA, are composed of deoxyadenosine (A), deoxycytidine (C), deoxyguanosine (G) and thymidine (T). These nucleotides can exhibit at least one of the following modifications: 2'-deoxy, 2'-fluorine, 2'-chlorine, 2'-bromine, 2'-iodine, 2'-amino (preferably non substituted or mono or di substituted), 2'-mono-, di- or tri-halo methyl, 2'-o-alkyl, 2'-o-halo-substituted alkyl, 2'-alkyl, azido, phosphorothioate, sulfhydryl, methylphosphonate, fluorescein, rhodamine, pyrene, biotine, xanthine, hypoxanthine, 2,6-diaminopurine, 2-hydroxy-6-mercaptopurine, polyethylene glycol modifications and for pyrimidine bases sulphur at 6-position and halogen at 5-position, $C_{1-5}$ alkyl groups, abasic linkers, 3'-deoxyadenosine or other chain terminators or non-extendable nucleotide analogues at 3'-end or other modifications at 5'- and/or 3'-end. Further modifications already disclosed in the state of the art such as e.g. in WO 02/26932 are of course comprised here as well.

In general, aptamers comprise 10 to 100 nucleotides, preferably 15 to 50 nucleotides, especially preferably 20 to 40 nucleotides. If necessary, aptamers exhibit a minimal sequence of at least 6, preferably at least 10 and especially preferably at least 14 to 15 nucleotides, which is necessary to guarantee the binding.

A preferred embodiment of the present invention are pharmaceutical preparations including at least one of the nucleic acids according to the invention.

An especially preferred embodiment of the present invention is the use of the nucleic acids, according to the invention, for the manufacture of a drug for the treatment of arteriosclerosis, wounds, AIDS, Alzheimer's disease, cancer, systemic lupus erythematosus, rheumatoid arthritis and other chronic inflammatory diseases, using the methods well known in the industry.

In a further preferred embodiment, the present invention also concerns the use of nucleic acids, according to the invention, as a diagnosis tool. Here, marked nucleic acids are used. The marking can be carried out e.g. with a fluorescent dye, an enzyme, antibody or a radionuclide. The corresponding detection methods are well known to the experts concerned.

Preferably, an aptamer, according to the invention, becomes a component part of a kit together with, for example, negative and positive controls. The expert knows very well that the corresponding aptamers, in principle, can be applied like antibodies e.g., in ELISA applications, chromatographic methods and for diagnostic/screening procedures.

Anti-apoptotically active, in the sense of the present invention, means that the corresponding substance in the inhibition test according to Example 6, causes an inhibition index of at least 50%, preferably at least 60%, especially preferably at least 70%, even more preferably at least 80%, even more preferably still at least 90% and most preferably of all at least 95% in relation to the control with TSP-1-induced apoptosis.

Aptamers, which are the active components of a pharmaceutical preparation, are usually dissolved in a suitable pharmaceutically acceptable vehicle. Examples for such pharmaceutically acceptable vehicles can be buffer solutions such as phosphate buffer or citrate buffer. For each patient, the specific dosing and posology is dependent on a number of factors including the activity of specific compounds used, the age of the patient, body weight, general state of health, the sex, nutrition, the time of administration, the method of administration, the excretion rate, the interaction with other medications, and the severity of the disease concerned for which the therapy is applied. This will be determined by a physician dependent on these factors.

Aptamer drugs are usually administered parentally e.g., with an inhalation spray, rectally, through subcutaneous, intravenous, intramuscular, intra-articular and intrathecal injection and infusion techniques, or externally in pharmaceutical preparations, which conventionally contain pharmaceutically acceptable media, adjuvants and vehicles. Depending on the nature of the identified substance, other means of administration are also possible e.g. orally. Furthermore, the drug can be applied as an ointment, gel, wet dressing etc.

The present invention also provides pharmaceutical compounds which contain an effective amount of an effective anti-apoptotic aptamer in combination with a conventional pharmaceutical vehicle. A pharmaceutical vehicle is e.g. a solid or liquid filler, an encapsulation material or a solvent. Examples for materials which can serve as pharmaceutical vehicles are sugars such as lactose, glucose and sucrose; starches such as maize starch and potato starch; cellulose and derivatives thereof such as sodium carboxymethyl cellulose, ethyl cellulose and cellulose acetate; powdered tragacanth; malt; gelatine; tallow; drug vehicles such as cocoa butter and suppository waxes; oils such as peanut oil, cotton seed oil, safflower oil, sesame oil, olive oil, maize oil and soybean oil; polyols such as propylene glycol, glycerol, sorbitol, mannitol and polyethylene glycol; esters such as ethyl oleate and ethyl laurate; agar; buffers such as magnesium hydroxide and aluminium hydroxide; alginic acid; pyrogen-free water; isotonic saline solution; Ringer's solution, ethanol and buffer phosphate solutions as well as other non-toxic compatible substances which are used in pharmaceutical preparations. Wetting agents, emulsifiers and lubricants such as sodium lauryl sulphate and magnesium stearate, as well as dyes, coating agents, perfumes and preserving agents can also be present in the preparations according to the requirements of the pharmaceutical technicians. The volume of the active substance which is combined with the vehicle materials in order to produce the individual dosage varies, depending on the patient being treated and the special method of administration.

Pharmaceutically suitable salts of the aptamers according to the present invention can be manufactured using the well known methods such as by dissolving the compounds, according to the present invention, in corresponding aqueous buffer solutions or $H_2O$ and subsequently freeze drying. Metallic salts can be obtained by dissolving the compounds, according to the present invention, in solutions which contain the corresponding ion and subsequently isolating the compound using HPLC or gel permeation methods.

Further procedures and methods for the manufacture of aptamer drugs as well as the administration thereof are e.g. disclosed in WO02/26932 and can of course be used here as well.

The nucleic acids, according to the present invention, can be manufactured in a simple manner, for example by conventional chemical synthesis using a DNA/RNA synthesizer, without presenting any problems to skilled staff in this field. The corresponding protocols and apparatus are well known to skilled staff in this field and are routine working.

EXAMPLES

Figure 1:
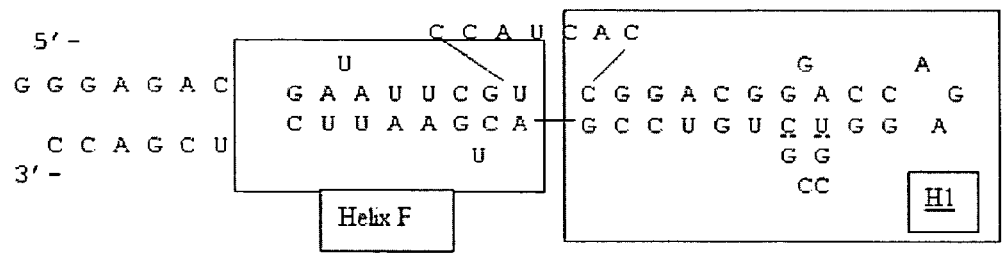
FIG. 1 shows a postulated secondary structure for SEQ ID NO: 2. Together with RNA sequence 5'-CGGAC GGGAC CAGAG GUGOC GCUGU CCG-3' (SEQ ID NO: 10) the aptamer SEQ ID NO: 2 forms the structure H1. This area with a helix (hairpin) structure (H1) is flanked by two RNA sections which can also form a helix structure called "helix F". The synthesis of changed/mutated RNAs starting from aptamer 89 (SEQ ID NO: 2) shows whether the flanking sequences, which form helix F, are important for the function of the aptamer and whether aptamer 89 can be shortened while still keeping its function (SEQ ID NO: 4, example 7).
Figure 2:
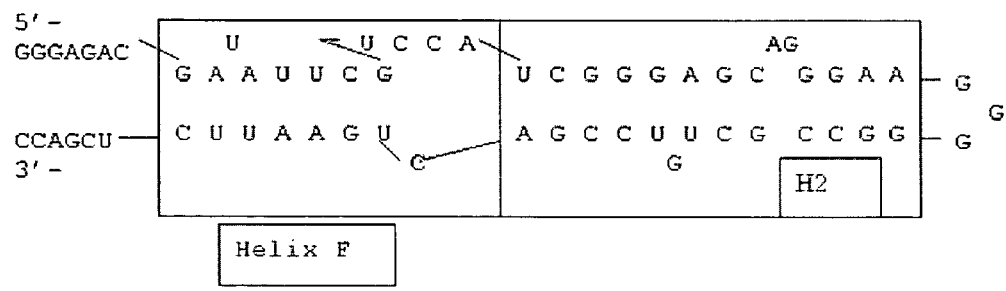
FIG. 2 shows a secondary structure calculated for SEQ ID NO: 7. In the central part of the sequence (SEQ ID NO: 9), the structure possesses a hairpin loop (H2) which is supplemented by a further helix from the flanking sequences.

The following examples exemplify the present invention without any limiting effect however.

The following overview shows the materials used and their supply sources. The sources are in Germany unless otherwise stated:

| Material | Company, Location | Order No. | Comment |
| --- | --- | --- | --- |
| Phenol | Carl Roth, Karlsruhe | 0038.1 | TE-equilibrated |
| T7-RNA polymerase | MBI-Fermentas, St. Leon-Roth | EP0111 | |
| ATP, GTP | Carl Roth, Karlsruhe | K045.1 K047.1 | |
| 2'-$NH_2$-UTP 2'-$NH_2$-CTP | tebu-bio, Offenbach | N-1027 N-1026 | Manufacturer: TriLink, San Diego, USA |
| RQ1 DNase I, RNase free | Promega, Mannheim | M6101 | |
| Chemicals, Biochemicals | Carl Roth, Karlsruhe Merck, Darmstadt; Sigma, Deisenhofen | | |

Double distilled water for preparing solutions was treated with diethyl pyrocarbonate (DEPC), 0.01% for 24 hours at 20 to 25° C. and subsequently autoclaved for 60 min at 121° C.

Solutions:

CI chloroform/isoamyl alcohol mixture 24:1 (volume/volume) 1×TBE90 mM Tris, 90 mM boric acid, 2 mM EDTA

Example 1

Synthesis of the Aptamers According to the Present Invention

Aptamer describes a modified RNA where the pyrimidine nucleotides (U and C) carry an $NH_2$— (amino) group at 2' position instead of the OH group. The synthesis of the modified RNA is performed here enzymatically using an RNA polymerase by insertion of unmodified purine and modified pyrimidine nucleotides.

Starting from double-stranded DNA (60-70 pmol DNA), which contains the T7 promoter sequence of the bacteriophage T7 and, from the first transcribed nucleotide, a DNA copy of the desired aptamer RNA (e.g. for aptamer no. 89: DNA sequence (SEQ ID NO: 1), beginning with 5'-GGGAGAC . . . -3', see example 2), the aptamer RNAs are synthesized by the T7 RNA polymerase. The transcription takes place in the presence of ATP and GTP as well as the modified nucleotides 2'-NH$_2$-UTP (2'NH$_2$-2'-deoxyuridine) and 2'-NH$_2$-CTP (2'NH$_2$-2'-deoxycytidine) by incubation with the commercial T7 RNA polymerase, under the buffer and salt conditions recommended by the manufacturer (Manufacturer: MBI-Fermentas, St. Leon-Roth), in a volume of 40 µl at 16° C.+/−3° C. for 20 to 44 hours. Then, the DNA which is still present is digested by adding MgCl$_2$ (increase of the concentration by 2.74 mM) and RNase-free DNase I (end concentration 0.06 units/µl) and incubation at 37° C. for 135 min, whereby 1 unit DNase I is defined as the enzyme volume which completely digests 1 µg DNA in 50 µl in buffer with 40 mM Tris-HCl, 10 mM NaCl, 6 mM MgCl$_2$, 10 mM CaCl$_2$, (pH 7.9 at 25° C.), in 10 minutes at 37° C.

After adding 45 µl TE buffer (10 mM Tris-HCl, 0.1 mM EDTA, pH 7.8), the solution is first extracted with phenol and then with chloroform/isoamyl alcohol (24:1). After this, the aptamer RNA is precipitated with ethanol and, after washing with 70% ethanol, is dissolved in 30 µl of DEPC-treated dd-H$_2$O and stored at −20° C. The yield of aptamer RNA is determined by analysis of the extinction at 260 and 280 nm, as well as together with nucleic acids of known concentration, after separation in a polyacrylamide gel in the presence of 8 M urea and Tris-boric acid buffer with 9.47% (w/v) acrylamide and 0.53% bis-acrylamide, 8 M urea and TBE buffer (standard 1×TBE buffer system: 90 mM Tris, 90 mM boric acid, 2 mM EDTA). The separation of the nucleic acids takes place at 12 to 16 V/cm for 35 to 45 min. The gel is then stained with the fluorescent dye SYBRGreen II (molecular probes; concentration according to manufacturer's instructions) for 20 min and excited with UV light and the fluorescence in visible light is analysed.

Example 2

Sequences of the Aptamers According to the Present Invention

1.) Sequences of DNA No. 89 (SEQ ID NO: 1)

5'-GGGAG ACGAT ATTCG TCCAT CACCG GACGG GACCA GAGGT GCCGC TGTCC GACTG AATTC TCGAC C-3'

2.) RNA sequence of the pyrimidine-modified aptamer No. 89 (SEQ ID NO: 2)

(U=2'-NH$_2$-2'-deoxyuridine; C=2'-NH$_2$-2'-deoxycytidine)

5'-GGGAG ACGAU AUUCG UCCAU CACCG GACGG GACCA GAGGU GCCGC UGUCC GACUG AAUUC UCGAC C-3'

3.) RNA sequence of the core area of the pyrimidine-modified aptamer No. 89 without flanking sequences (SEQ ID NO: 3)

(U=2'-NH$_2$-2'-deoxyuridine; C=2'-NH$_2$-2'-deoxycytidine)

5'-ACCGG ACGGG ACCAG AGGUG C-3'

4.) RNA sequence of the aptamer mutant "89-2" (58 nt) (SEQ ID NO: 4)

(U=2'-NH$_2$-2'-deoxyuridine; C=2'-NH$_2$-2'-deoxycytidine)

5'-GGGAG ACGAU AUUCG UCCAU CACCG GACGG GACCA GAGGU GCCGC UGUCC GACAU GGA-3'

5.) RNA sequence of the aptamer mutant No. 89-Z (30 nt) (SEQ ID NO: 5)

(U=2'-NH$_2$-2'-deoxyuridine; C=2'-NH$_2$-2'-deoxycytidine)

5'-ACCGG ACGGG ACCAG AGGUG CCGCU GUCCG-3'

6.) Sequence of DNA No. 82 (SEQ ID NO: 6)

5'-GGGAG ACGAT ATTCG TCCAT CGGGA GCAGG GAAGG GGGCC GCTGT CCGAC TGAAT TCTCG ACC-3'

7.) RNA sequence of the pyrimidine-modified aptamer No. 82 (SEQ ID NO: 7)

(U=2'-NH$_2$-2'-deoxyuridine; C=2'-NH$_2$-2'-deoxycytidine)

5'-GGGAG ACGAU AUUCG UCCAU CGGGA GCAGG GAAGG GGGCC GCUGU CCGAC UGAAU UCUCG ACC-3'

8.) RNA sequence of the core area of the pyrimidine-modified aptamer No. 82 without flanking sequences (SEQ ID NO: 8)

(U=2'-NH$_2$-2'-deoxyuridine; C=2'-NH$_2$-2'-deoxycytidine)

5'-GGGAG CAGGG AAGGG GGC-3'

9.) RNA sequence of the aptamer mutant No. 82-Z (30 nt) (SEQ ID NO: 9)

(U=2'-NH$_2$-2'-deoxyuridine; C=2'-NH$_2$-2'-deoxycytidine)

5'-UCGGG AGCAG GGAAG GGGGC CGCUG UCCGA-3'

Example 3

Cultivation of Human Endothelial Cells from Umbilical Veins (HUVEC)

Solutions (Sterile):

Culture medium: IF Basal Medium+15% (v/v) NCS, 5 µg/ml transferrin, 5 µg/ml heparin, 0.7 µg/ml FGF, 2 mM L-glutamine [IF Basal Medium: 1:1-mixture of Iscove's Modified Dulbecco Medium (IMDM) and Ham's F12, both from Life Technologies, Paisley (Great Britain)]

NCS: New-born calf serum (Sebak, Aidenbach)

FGF: Fibroblast growth factor (own production, partially purified from porcine brain)

Materials

Cell culture vessels, gelatin-coated

Experimental Procedure:

The cultivation of HUVEC is carried out in gelatin-coated culture vessels at 37° C. in a 5% CO$_2$ and steam-saturated air atmosphere. The culture medium is changed every 2-3 days; at confluence the cells are passaged with a separation rate of 1:3 to 1:5. HUVEC grow strictly contact-inhibited and form single-layer cell lawns with the typical cobblestone morphology. At confluence, the cultures reach cell densities of 4-9×

10⁴ cells/cm². For apoptosis examinations, HUVEC cultures of the passages 1-4 are used exclusively.

Coating of Culture Vessels:
Solutions (Sterile):
Gelatin solution, 1% (w/v) in Milli-Q Water
Suspend 1 g of gelatin (cell culture tested) in 100 ml Milli-Q water, dissolve by autoclaving for 20 min at 121° C. and 2 bar and store at room temperature.
PBS (140 mM NaCl, 3 mM KCl, 8 mM $Na_2HPO_4$, 1.5 mM $KH_2PO_4$)
8 g/l NaCl
0.2 g/l KCl
1.44 g/l $Na_2HPO_4 \times 2\ H_2 0$
0.2 g/l $KH_2PO_4$
Dissolve the salts in a corresponding volume of Milli-Q water, autoclave for 20 min at 121° C. and 2 bar, store at room temperature. The pH value is measured and lies between 7.2 and 7.4.
Materials:
Cell culture vessels
Experimental Procedure:
Culture vessels are coated with gelatin for the cultivation of adherently growing cells. The bottoms of the cell culture vessels are covered with sterile gelatin solution and the vessels are left to stand for 15 minutes at room temperature. The gelatin solution is suctioned off. The cell culture vessels are washed once with PBS and can then be used.

Subcultivation of adherent cells
Solutions (sterile):
PBS
Trypsin/EDTA (0.05% (w/v)/0.02% (w/v))
0.1 ml trypsin stock solution
0.05 ml EDTA stock solution
Fill up to 50 ml with sterile PBS and store in potions of 10 ml at −20° C.
Materials:
Cell culture vessels, gelatined
Experimental Procedure:
All cell types are detached from the culture surface with trypsin/EDTA solution. The culture medium is removed by suction. The bottom of the culture vessel is briefly washed with PBS and then covered with trypsin/EDTA solution (~1 ml for a 25 cm² culture flask). The enzyme solution is immediately suctioned off again so that a thin liquid film remains on the cells. The cells are left to stand at room temperature for 1-10 min and the detachment of the cells is observed under the microscope. The detachment of the cells can be accelerated by gently tapping the culture vessel on the edge. The cells are transferred to fresh culture medium, if required counted, and then seeded out in new culture vessels.

Example 4

Determination of the Apoptosis Rate by Staining Apoptotic Cells with DAPI

DAPI belongs to the indole dyes group and provides a selective DNS stain. The stain is excited at 340-360 nm with an emission maximum of 480 nm. The substance is used for apoptosis examinations [compare: Cohen et al., Immunology Today, 14, NO. 3, 126-130 (1993)].
Morphological Evaluation:
Solutions:
PBS
Formaldehyde solution
4% (v/v) formaldehyde in PBS
DAPI solution (Molecular Probes, Leiden, Netherlands) 2 µg/ml DAPI in methanol
Materials:
Petri dish (35 mm) or 24 well plate with HUVEC cell in culture
Experimental Procedure:
The culture supernatant of a Petri dish or 24 well plate is suctioned off. The cell-lawn is fixed for 15 minutes with 1 ml formaldehyde solution cooled on ice, washed twice with 2 ml PBS. 0.5 ml DAPI solution is added for 15 minutes, then washed again with PBS and evaluated under the fluorescence microscope. This work is carried out with a UV filter set and a 20× or 40× objective. 500-1000 cells are chosen at random and the number with apoptotic nuclei are counted.
The apoptosis index is calculated according to the following formula:

Apoptosis index[%]=number of apoptotic cells/total cell count×100

Example 5

Testing System for Anti-apoptotically Active Aptamers

The cells are cultivated in the manner described in example 3. The cells are seeded in appropriate culture vessels (e.g., 24 well plate/0.5 ml per well) and after reaching complete confluence they can be used for the actual test.

The induction of apoptosis is carried out by TSP 1, which endothelial cells produce and secrete themselves, and which is enriched in the culture medium (autoconditioning of the culture medium).

Examinations are carried out to establish the influence of the various aptamers on the apoptosis rate of endothelial cells. For these, the aptamers, which are dissolved in DEPC-treated double distilled water (example 1), are diluted in the in the culture medium for HUVEC (example 3) and used at the given concentrations. Culture medium without any aptamers or inhibitors whatsoever is used as a positive control.

The medium with the aptamers is added to the cells and incubated for three days under culture conditions (example 3). After 36 hours, the culture medium/culture medium with aptamers is changed once.

Subsequently, the cells, as described in example 4, are stained with DAPI to determine the apoptosis rate and the apoptosis index is calculated with the given formula.

The clearly apoptosis-inducing action of the autoconditioned medium in the case of the positive control, and the reduced apoptosis in the case of the inhibition control, demonstrate the success of the test as an internal control.

Example 6

Identification of Anti-apoptotically Active Aptamers Using the Method According to the Present Invention The cells are cultivated in the manner described in example 3. The cells are seeded in appropriate culture vessels (e.g. 24 well plate/0.5 ml per well) and after reaching complete confluence they can be used for the test according to example 4. The following samples are prepared:
(K) Culture medium [autoconditioned medium, basis rate of apoptosis, control],
(1) Culture medium+aptamer 89, SEQ ID NO 2, concentration: 150 nM (2) Culture medium+aptamer 89, SEQ ID NO 2, concentration: 300 nM (3) Culture medium+aptamer 82, SEQ ID NO 7, concentration: 150 nM (4) Culture medium+aptamer 82, SEQ ID NO 7, concentration: 300 nM After 72 hours of incubation under culture conditions, the cells are fixed, stained with DAPI, and examined morphologically under a fluorescence microscope. The apoptotic cell count and the total cell count are determined and the apoptosis index is calculated (percentage of apoptotic cells) (example 3, example 4, example 5).

TABLE 1

The following aptamers were tested. The corresponding sequences are given in example 2.:

| Sample No. | Aptamer designation | Apoptosis index [%] | Inhibition index [%]* |
|---|---|---|---|
| K | Control | 3.59 ± 0.54 | — |
| (1) | 89, 150 nM | 0.17 ± 0.15 | 95.24 |
| (2) | 89, 300 nM | 0.16 ± 0.14 | 95.65 |
| (3) | 82, 150 nM | 1.22 ± 0.27 | 66.03 |
| (4) | 82, 300 nM | 0.74 ± 0.19 | 79.32 |

*100% = no further apoptosis determinable; 0% = no effect = control

Example 7

Identification of the Minimized Sequence of the Anti-apoptotically Active Aptamers by Shortening The test was carried out as described in example 6. An aptamer with a reduced total length (SEQ ID NO 4, called here "89-2") was compared with Aptamer 89 (full length SEQ ID NO 2, called "89"). The thermodynamically preferred hairpin structure HI also forms for SEQ ID NO 4—as shown in FIG. 1. In contrast, the existing sequence 5'-UGAAUU-CUCGACC-3' at the 3' end of SEQ ID NO 2 replaced at SEQ ID NO 4 by the RNA sequence 5'-AUGGA-3' (modified RNA, see example 2). This destroys the structure of "Helix F" and a new short helix can form (5'-AUGGA/5'-UCCAU).

The cells are cultivated in the manner described in example 3. The cells are seeded in appropriate culture vessels (e.g. 24 well plate/0.5 ml per well) and after reaching complete confluence they can be used for the test. (example 4, example 5). The following sample are prepared:

(K) Culture medium [autoconditioned medium, basis rate of apoptosis, control], (5) Culture medium+aptamer 89, SEQ ID NO 2, concentration: 50 nM (6) Culture medium+aptamer 89, SEQ ID NO 4, concentration: 50 nM The following Table 2 summarizes the results. It is clearly recognisable that the shortened sequence area in No. 89-2 (SEQ ID NO 4) has an activity comparable to that of the original sequence No. 89 (SEQ ID NO 2).

TABLE 2

The following aptamers were tested. The corresponding sequences are presented in example 2:

| Sample No. | Aptamer designation | Apoptosis index [%] | Inhibition Index [%]* |
|---|---|---|---|
| K | control | 4.99 ± 0.59 | — |
| (5) | 89 | 0.44 ± 0.21 | 91.15 |
| (6) | 89-2 | 0.81 ± 0.30 | 83.76 |

*100% = no further apoptosis determinable; 0% = no effect = control

The invention claimed is:

1. An isolated nucleic acid having the nucleic acid sequence selected from the group consisting of SEQ ID NO: 1, SEQ ID NO: 4, and SEQ ID NO: 2.

2. An isolated nucleic acid comprising the nucleic acid sequence having at least 90% sequence identity to SEQ ID NO: 1 or SEQ ID NO: 2.

3. The isolated nucleic acid of claim 2, wherein the nucleic acid sequence has at least 95% sequence identity to SEQ ID NO: 1 or SEQ ID NO: 2.

4. A pharmaceutical preparation comprising the isolated nucleic acid of claim 2 in combination with a pharmaceutical vehicle.

5. A diagnostic test kit comprising the isolated nucleic acid of claim 2 in combination with positive and negative controls.

6. A method of manufacturing the isolated nucleic acid of claim 2, comprising chemically synthesizing the nucleic acid using a DNA/RNA synthesizer.

* * * * *